United States Patent [19]

Lee

[11] Patent Number: 4,780,569
[45] Date of Patent: Oct. 25, 1988

[54] CERTAIN 1,3-DIPHENYL-1,3-PROPANEDIONES

[75] Inventor: David L. Lee, Martinez, Calif.

[73] Assignee: Stauffer Chemical Company, Westport, Conn.

[21] Appl. No.: 872,347

[22] Filed: Jun. 9, 1986

[51] Int. Cl.⁴ .......................................... C07C 49/213
[52] U.S. Cl. ................................. 568/306; 558/415;
558/411; 558/412; 558/413; 558/414; 558/417;
564/221; 564/440; 564/441; 564/442; 564/443;
564/305; 564/85; 564/87; 564/88; 568/42;
568/43; 568/331; 71/121; 71/118; 71/105;
71/107; 71/111
[58] Field of Search ............... 568/331, 306, 42, 43;
560/51; 71/123, 105, 121, 118, 103, 107, 111;
558/415, 411, 412, 413, 414, 417; 564/305, 440,
441, 442, 443, 221, 85, 87, 88

[56] References Cited

U.S. PATENT DOCUMENTS 2,417,381  3/1947  Spence et al. .................... 568/331
2,472,628  6/1949  Spence et al. .................... 568/331

FOREIGN PATENT DOCUMENTS 2813341  10/1978  Fed. Rep. of Germany ...... 568/331
51-111252  10/1976  Japan ................................... 568/331

OTHER PUBLICATIONS

Romas et al, Zh. Org. Khim, vol. 21(11), pp. 2073–2077 (1985).

Bayne et al, J. Chem. Soc, Chem. Comm., 1975, pp 782–783.

Primary Examiner—James H. Reamer
Attorney, Agent, or Firm—Edwin H. Baker

[57] ABSTRACT

Compounds of the formula

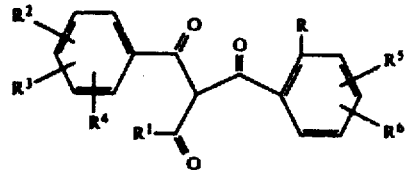

wherein
R is hydrogen; halogen; $C_1$–$C_2$ alkyl; $C_1$–$C_2$ alkoxy; nitro; cyano; $C_1$–$C_2$ haloalkyl; or $R^aSO_n$- wherein n is 0 or 2 and $R^a$ is $C_1$–$C_2$ alkyl;
$R^1$ is $C_1$–$C_4$ alkyl or $C_1$–$C_4$ alkoxy;
$R^2$, $R^3$, $R^4$, $R^5$ and $R^6$ independently are (1) hydrogen; (2) halogen; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^bSO_n$- wherein n is the integer 0, 1 or 2; and $R^b$ is (a) $C_1$–$C_4$ alkyl; (b) $C_1$–$C_4$ alkyl substituted with halogen or cyano; (c) phenyl; or (d) benzyl; (10) —$NR^cR^d$ wherein $R^c$ and $R^d$ independently are hydrogen or $C_1$–$C_4$ alkyl; (11) $R^eC(O)$- wherein $R^e$ is $C_1$–$C_4$ alkyl or $C_1$–$C_4$ alkoxy; or (12) —$SO_2NR^cR^d$ wherein $R^c$ and $R^d$ are as defined; and (13) —$N(R^c)$-$C(O)R^d$ wherein $R^c$ and $R^d$ are as defined and their salts.

13 Claims, No Drawings

CERTAIN 1,3-DIPHENYL-1,3-PROPANEDIONES

DESCRIPTION OF THE INVENTION

This invention relates to 1,3-diphenyl-1,3-propanediones and their use as herbicides.

One embodiment of this invention is an herbicidal composition comprising an herbicidally active 1,3-diphenyl-1,3-propanedione or their salts and an inert carrier therefor. The 2-position of the 1,3-propanedione moiety is preferably substituted with $C_1$-$C_4$ alkyl—C(O)— or $C_1$-$C_4$ alkoxy—C(O)— groups. The phenyl moieties can be substituted, preferably with the groups hereinafter recited.

Also embodied within the scope of this invention are novel compounds having the following structural formula

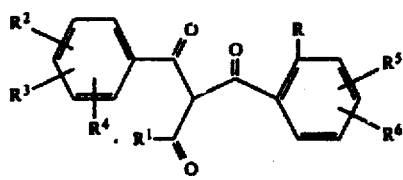

wherein

R is hydrogen; halogen; $C_1$-$C_2$ alkyl, preferably methyl; $C_1$-$C_2$ alkoxy, preferably methoxy; nitro; cyano; $C_1$-$C_2$ haloalkyl, preferably trifluoromethyl; or $R^aSO_n$— wherein n is 0 or 2, preferably 2 and $R^a$ is $C_1$-$C_2$ alkyl, preferably methyl. Preferably, R is chlorine, bromine, $C_1$-$C_2$ alkyl, $C_1$-$C_2$ alkoxy, trifluoromethyl, cyano, nitro, $C_1$-$C_2$ alkylthio or $C_1$-$C_2$ alkylsulfonyl; more preferably chlorine, nitro, methyl, trifluoromethyl or methylsulfonyl; and $R^1$ is $C_1$-$C_4$ alkyl, preferably $C_1$-$C_2$ alkyl, more preferably methyl or $C_1$-$C_4$ alkoxy, preferably $C_1$-$C_2$ alkoxy, more preferably ethoxy;

$R^2$, $R^3$, $R^4$, $R^5$ and $R^6$ independently are (1) hydrogen; (2) halogen, preferably chlorine, fluorine or bromine; (3) $C_1$-$C_4$ alkyl, preferably methyl; (4) $C_1$-$C_4$ alkoxy, preferably methoxy; (5) trifluoromethoxy; (6) cyano; (7) nitro; (8) $C_1$-$C_4$ haloalkyl, more preferably trifluoromethyl; (9) $R^bSO_n$— wherein n is the integer 0, 1 or 2, preferably 2; and $R^b$ is (a) $C_1$-$C_4$ alkyl, preferably methyl;
(b) $C_1$-$C_4$ alkyl substituted with halogen or cyano, preferably chloromethyl, trifluoromethyl or cyanomethyl;
(c) phenyl; or
(d) benzyl;

(10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; (12) —$SO_2NR^cR^d$ wherein $R^c$ and $R^d$ are as defined; or (13) —$N(R^c)C(O)R^d$ wherein $R^c$ and $R^d$ are as defined.

Preferably $R^2$ is 2-nitro or 2-chlorine; $R^3$ is hydrogen and $R^4$ is hydrogen.

Preferably $R^5$ is in the 3-position. More preferably $R^5$ is hydrogen, chlorine, fluorine, trifluoromethyl, cyano, $C_1$-$C_4$ alkoxy or $C_1$-$C_4$ thioalkyl. Most preferably, $R^5$ is hydrogen. Preferably $R^6$ is in the 4-position. Most preferably $R^6$ is halogen, cyano, trifluoromethyl, or $R^bSO_2$ wherein $R^b$ is $C_1$-$C_4$ alkyl, preferably methyl or $C_1$-$C_4$ haloalkyl, preferably chloromethyl, difluoromethyl or trifluoromethyl.

The term "$C_1$-$C_4$ alkyl" includes methyl, ethyl, n-propyl, isopropyl, n-butyl, sec-butyl, isobutyl and t-butyl. The term "halogen" includes chlorine, bromine, iodine and fluorine. The terms "$C_1$-$C_4$ alkoxy" includes methoxy, ethoxy, n-propoxy, isopropoxy, n-butoxy, sec-butoxy, isobutoxy and t-butoxy. The term "$C_1$-$C_4$ haloalkyl" includes the alkyl groups defined above under $C_1$-$C_4$ alkyl in which one or more hydrogen is replaced by chlorine, bromine, iodine or fluorine.

Salts of the above-described compounds (as defined hereinafter) are included within the scope of the instant invention.

The compounds of this invention can have the following four structural formulae because of tautomerism:

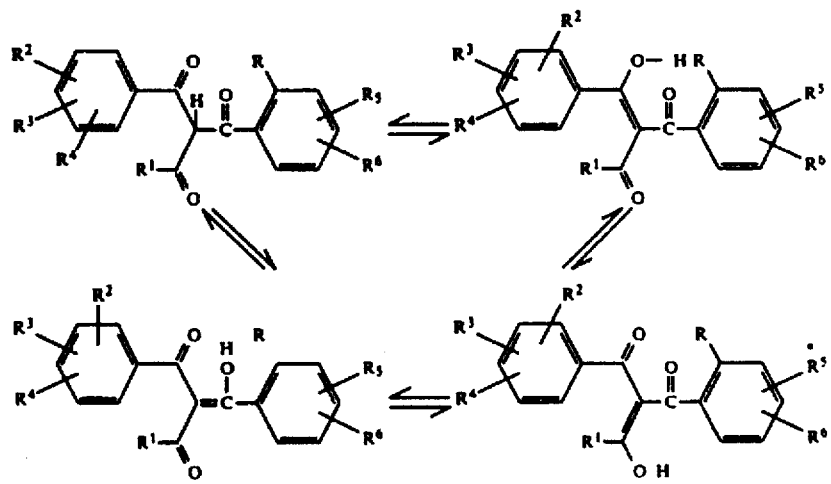

*Exists only when $R^1$ is $C_1$-$C_4$ alkyl.

wherein R, $R^1$, $R^2$, $R^3$, $R^4$, $R^5$ and $R^6$ are as defined above.

The circled proton on each of the four tautomers is reasonably labile. These protons are acidic and can be removed by reaction with a base to form a salt having an anion of the following four resonance forms:

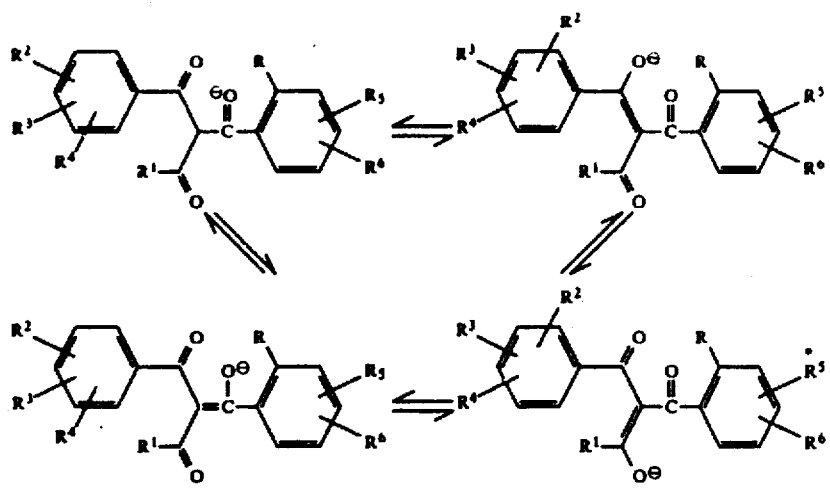

*Exists only when R¹ is $C_1$-$C_4$ alkyl wherein R, $R^1$, $R^2$, $R^3$, $R^4$, $R^5$ and $R^6$ are as defined above.

Examples of cations of these bases are inorganic cations such as alkali metals, e.g. lithium, sodium and potassium; the alkaline earth metals, e.g. calcium and magnesium or ammonium or organic cations such as substituted ammonium, sulfonium, sulfoxonium or phosphonium wherein the substituents are aliphatic or aromatic groups.

Those skilled in the art will recognize in considering the salts of this invention that varying degrees of association between the anion and cation will exist depending upon the nature of the cation. In some instances with a suitable cation, such as copper, the salt can exist in a chelated form.

The compounds of this invention and their salts are active herbicides of a general type. That is, they are herbicidally effective against a wide range of plant species. The method of controlling undesirable vegetation of the present invention comprises applying an herbicidally effective amount of the above-described compounds or their salts to the area where control is desired.

The compounds of the present invention can be prepared by the following general method.

The various substituted benzoyl acetones can be obtained from the requisite substituted phenyl acetic acids or phenyl acetonitriles by methods taught in C. A. Buehler and D. E. Pearson, *Survey of Organic Syntheses*, Vol. I, Chapter 11 (1970).

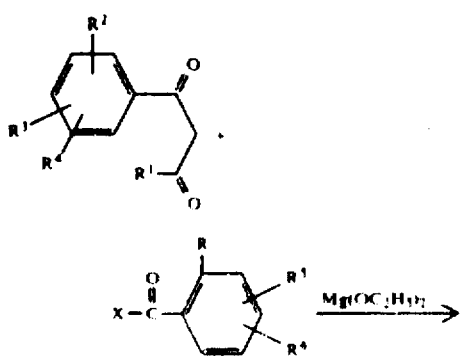

-continued wherein R through $R^6$ are as defined and X is halogen, preferably chlorine.

Generally, mole amounts of the dione, magnesium ethoxide, and substituted benzoyl chloride are used. The dione and magnesium ethoxide are combined in a solvent such as diethyl ether and heated at reflux for 1 hour. The benzoyl chloride is then slowly added, and the reaction mixture is heated at reflux for another 0.5–1 hour. The reaction product is worked up by conventional techniques.

The above described substituted benzoyl chlorides can be prepared from the corresponding substituted benzoic acids according to the teaching of *Reagents for Organic Synthesis*, Vol. I, L. F. Fieser and M. Fieser, pp. 767–769 (1967).

wherein R, $R^5$ and $R^6$ are as previously defined.

The substituted benzoic acids can be prepared by a wide variety of general methods according to the teaching of *The Chemistry of Carboxylic Acids and Esters*, S. Patai, editor, J. Wiley and Sons, New York, N.Y. (1969) and *Survey of Organic Synthesis*, C. A. Buehler and D. F. Pearson, J. Wiley and Sons, (1970).

The following are three representative examples of the methods described therein.

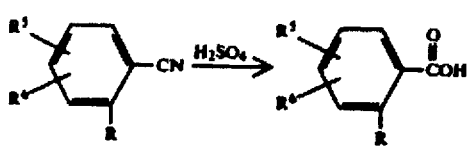

wherein R, R⁵ and R⁶ are as previously defined.

In reaction (a) the substituted benzonitrile is heated to reflux in aqueous sulfuric acid for several hours. The mixture is cooled and the reaction product is isolated by conventional techniques.

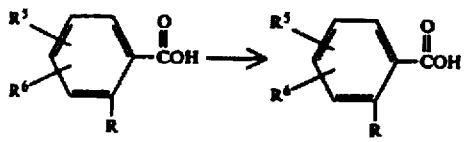

wherein R, R⁵ and R⁶ are as previously defined.

In reaction (b) the substituted acetophenone is heated to reflux for several hours in an aqueous hypochlorite solution. The mixture is cooled and the reaction product is isolated by conventional techniques.

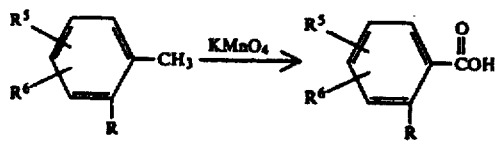

wherein R, R⁵ and R⁵ are as previously defined.

In reaction (c) the substituted toluene is heated to reflux in an aqueous solution of potassium permanganate for several hours. The solution is then filtered and the reaction product is isolated by conventional techniques.

The following example teaches the synthesis of a representative compound of this invention.

EXAMPLE 1

2-Acetyl-1-(2-nitrophenyl)-3-phenyl-1,3-propanedione

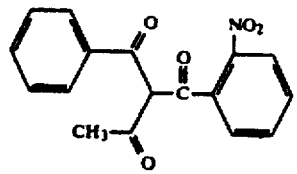

A mixture of benzoylacetone (8.1 g, 0.05 mole), magnesium ethoxide (5.7 g, 0.05 mole) and ethyl ether (100 ml) was heated at reflux for 1 hour. The reaction mixture was cooled to room temperature, and 2-nitrobenzoyl chloride (11.1 g, 0.06 mole) was added dropwise over a period of 15 minutes. The reaction mixture was then heated at reflux for 1 hour. After cooling to room temperature, the reaction mixture was poured into 50 ml of 2N hydrochloric acid, and the phases separated. The ether layer was extracted with 5% potassium carbonate. The basic extract was acidified with hydrochloric acid and extracted with ether. The ether extract was washed with saturated sodium chloride, dried over magnesium sulfate and concentrated under vacuum yielding 11.4 g of the desired product as a white solid with a melting point of 99°-103° C. It was identified as such by nuclear magnetic resonance spectroscopy, infrared spectroscopy and mass spectroscopy.

The following is a table of certain selected compounds that are preparable according to the procedure described hereto. Compound numbers are assigned to each compound and are used throughout the remainder of the application.

TABLE I

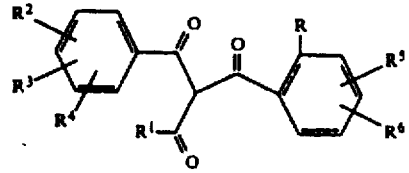

| Comp. No. | R | R¹ | R² | R³ | R⁴ | R⁵ | R⁶ | m.p. °C |
|---|---|---|---|---|---|---|---|---|
| 1 | Cl | C₂H₅O | H | H | H | H | 4-Cl | oil |
| 2 | Cl | CH₃ | H | H | H | H | 4-SO₂CH₃ | semi-solid |
| 3 | NO₂ | CH₃ | H | H | H | H | 4-Cl | oil |
| 4* | NO₂ | CH₃ | H | H | H | H | H | 99-103 |
| 5 | CH₃ | CH₃ | H | H | H | H | 4-SO₂C₂H₅ | 136-140 |
| 6 | Cl | CH₃ | H | H | H | 3-Cl | 4-SO₂C₂H₅ | 144-151 |
| 7 | Cl | CH₃ | 2-NO₂ | H | H | H | 4-Cl | oil |
| 8 | NO₂ | CH₃ | 2-Cl | H | H | H | H | 94-102 |
| 9 | NO₂ | CH₃ | 2-NO₂ | H | H | H | H | 163-166 |
| 10 | NO₂ | CH₃ | 2-Cl | H | H | H | 4-Cl | 117-126 |

*prepared in Example 1

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence herbicide test. On the day preceding treatment, seeds of seven different weed species are planted in loamy sand soil in individual rows using one species per row across the width of a flat. The seeds used are green foxtail (FT) (*Setaria viridis*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*), and yellow nutsedge (YNG) (*Cyperus esculentus*). Ample seeds are planted to give about 20 to 40 seedlings per row, after emergence, depending upon the size of the plants.

Using an analytical balance, 600 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rate from 0 to 100% is recorded for each species as percent control with 0% representing no injury and 100% representing complete control.

The results of the tests are shown in the following Table II.

TABLE II

| Pre-Emergence Herbicidal Activity - Application Rate - 4.48 kg/ha | | | | | | | |
|---|---|---|---|---|---|---|---|
| Cmpd. No. | FT | WG | WO | AMG | VL | MD | YNG |
| 1 | 40 | 20 | 0 | 60 | 95 | 85 | 70 |
| 2 | 90 | 100 | 75 | 100 | 100 | 100 | 80 |
| 3 | 95 | 100 | 80 | 20 | 100 | 100 | 80 |
| 4 | 100 | 100 | 90 | 20 | 100 | 100 | 80 |
| 5 | 100 | 100 | 95 | 100 | 100 | 100 | 100 |
| 6 | 10 | 85 | 70 | 100 | 100 | 100 | 80 |
| 7 | 50 | 95 | 0 | 0 | 100 | 100 | 10 |
| 8 | 80 | 80 | 80 | 10 | 80 | 100 | 70 |
| 9 | 75 | 85 | 85 | 20 | 90 | 100 | 70 |
| 10 | 80 | 40 | 40 | 0 | 100 | 100 | 60 |

A blank (-) indicates that the weed was not tested.

Post-Emergence Herbicide Test: This test is conducted in an identical manner to the testing procedure for the pre-emergence herbicide test, except the seeds of the seven different weed species are planted 10–12 days before treatment. Also, watering of the treated flats is confined to the soil surface and not to the foliage of the sprouted plants.

The results of the post-emergence herbicide test are reported in Table III.

TABLE III

| Post-Emergence Herbicidal Activity · Application Rate · 4.48 kg/ha | | | | | | | |
|---|---|---|---|---|---|---|---|
| Cmpd. No. | FT | WG | WO | AMG | VL | MD | YNG |
| 1 | 20 | 65 | 20 | 45 | 90 | 90 | 10 |
| 2 | 30 | 50 | 20 | 20 | 80 | 80 | 10 |
| 3 | 40 | 50 | 40 | 70 | 80 | 100 | 10 |
| 4 | 100 | 60 | 70 | 70 | 90 | 90 | 10 |
| 5 | 90 | 70 | 70 | 90 | 85 | 90 | 10 |
| 6 | 50 | 80 | 30 | 100 | 100 | 95 | 10 |
| 7 | 80 | 70 | 0 | 20 | 90 | 100 | 70 |
| 8 | 50 | 30 | 40 | 50 | 80 | 80 | 10 |

TABLE III-continued

| Post-Emergence Herbicidal Activity Application Rate · 4.48 kg/ha | | | | | | | |
|---|---|---|---|---|---|---|---|
| Cmpd. No. | FT | WG | WO | AMG | VL | MD | YNG |
| 9 | 20 | 30 | 50 | 60 | 80 | 80 | 70 |
| 10 | 10 | 20 | 20 | 10 | 60 | 60 | 30 |

A blank (-) indicates the weed was not tested.

The compounds of the present invention and their salts are useful as herbicides and can be applied in a variety of ways at various concentrations. In practice, the compounds or salts are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds or salts can be formulated as granules of relatively large particle size, as wettable powders, as emulsifiable concentrates, as powdery dusts, as flowables, as solutions or as any of several other known types of formulations, depending upon the desired mode of application. These formulations may contain as little as about 0.5% to as much as about 95% or more by weight of active ingredient. A herbicidally effective amount depends upon the nature of the seeds or plants to be controlled and the rate of application varies from about 0.01 to approximately 10 pounds per acre, preferably from about 0.02 to about 4 pounds per acre.

Wettable powders are in the form of finely divided particles which disperse readily in water or other dispersants. The wettable powder is ultimately applied to the soil either as a dry dust or as a dispersion in water or, other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound or salt with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which may be coated with the toxicant. Granular formulations normally are prepared to contain about 5% to about 25% of active ingredients which may include surface-active agents such heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their salts; polyhydric alcohols; polyethoxylated alcohols; esters and fatty amines; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated napthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of the invention can be applied to the plants in the conventional manner. Thus, the dust and liquid compositions can be applied to the plant by the use of power-dusters, boom and hand sprayers and spray dusters. The compositions can also be applied from airplanes as a dust or a spray or by rope wick applications because they are effective in very low dosages. In order to modify or control growth of germinating seeds or emerging seedlings, as a typical example, the dust and liquid compositions can be applied to the soil according to conventional methods and can be distributed in the soil to a depth of at least ¼ inch below the soil surface. It is not necessary that the phytotoxic compositions be mechanically admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be destributed below the surface of the soil by conventional means such as discing, dragging or mixing operations. In the following examples the herbicidal compound can be substituted with the herbicidal salt of the compound.

| General Formula with Ranges | | Specific Formula | |
|---|---|---|---|
| EMULSIFIABLE CONCENTRATE FORMULATIONS | | | |
| Herbicidal compound | 5–55 | herbicidal compound | 24 |
| surfactant(s) | 5–25 | proprietary blend of oil-soluble | 10 |
| solvent(s) | 20–90 | sulfonates and polyoxyethylene ethers | |
| | 100% | polar solvent | 27 |
| | | petroleum hydrocarbon | 39 |
| | | | 100% |
| WETTABLE POWDER FORMULATIONS | | | |
| herbicidal compound | 3–90 | herbicidal compound | 80 |
| wetting agent | 0.5–2 | sodium dialkyl naphthalene sulfonate | 0.5 |
| dispersing agent | 1–8 | sodium lignosulfonate | 7 |
| diluent(s) | 8.5–87 | attapulgite clay | 12.5 |
| | 100% | | 100% |
| EXTRUDED GRANULAR FORMULATIONS | | | |
| herbicidal compound | 1–20 | herbicidal compound | 10 |
| binding agent | 0–10 | lignin sulfonate | 5 |
| diluent(s) | 70–99 | calcium carbonate | 85 |
| | 100% | | 100% |
| FLOWABLE FORMULATIONS | | | |
| herbicidal compound | 20–70 | herbicidal compound | 45 |
| surfactant(s) | 1–10 | polyoxyethylene ether | 5 |
| suspending agent(s) | 0.05–1 | attagel | 0.05 |
| antifreeze agent | 1–10 | propylene glycol | 10 |
| antimicrobial agent | 1–10 | 1,2-benzisothiazoline-3-one | 0.03 |
| antifoam agent | 0.1–1 | silicone defoamer | 0.02 |
| solvent | 7.95–77.85 | water | 39.9 |
| | 100% | | 100% |

When salts are used as the active ingredient in the herbicidal compositions of this invention it is recommended to use salts that are agriculturally acceptable.

The phytotoxic of this invention can also contain other additives, for example, fertilizers, other herbicides and other pesticides, used as adjuvant or in combination with any of the abovedescribed adjuvants. Fertilizers useful in combination with the active ingredients include, for example, ammonium nitrate, urea and superphosphate.

What is claimed is:

1. Compounds of the formula

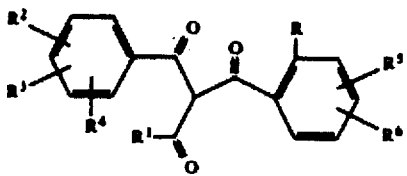

wherein

R is hydrogen; halogen; $C_1$-$C_2$ alkyl; $C_1$-$C_2$ alkoxy; nitro; cyano; $C_1$-$C_2$ haloalkyl; or $R^aSO_n$— wherein n is 0 or 2 and $R^a$ is $C_1$-$C_2$ alkyl;

$R^1$ is $C_1$-$C_4$ alkyl or $C_1$-$C_4$ alkoxy;

$R^2$, $R^3$, $R^4$, $R^5$ and $R^6$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^cC(O)$— wherein $R^c$ is $C_1$-$C_4$ alkyl or $C_1$-$C_4$ alkoxy; or (12) —$SO_2NR^cR^d$ wherein $R^c$ and $R^d$ are as defined; and (13) —$N(R^c)C(O)R^d$ wherein $R^c$ and $R^d$ are as defined and their salts.

2. The compounds of claim 1 wherein R is chlorine, hydrogen, bromine, methyl, methoxy, nitro, trifluoromethyl or methylsulfonyl; $R^1$ is $C_1$-$C_2$ alkyl or $C_1$-$C_2$ alkoxy; $R^2$, $R^3$, $R^4$, $R^5$ and $R^6$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^cC(O)$— wherein $R^c$ is $C_1$-$C_4$ alkyl or $C_1$-$C_4$ alkoxy; or (12) $SO_2NR^cR^d$ and wherein $R^c$ and $R^d$ are as defined; or (13) —N—($R^c$)-$C(O)R^d$ wherein $R^c$ and $R^d$ are as defined.

3. The compounds of claim 2 wherein $R^2$ is chlorine or nitro; $R^3$ is hydrogen, $R^4$ is hydrogen and $R^5$ and $R_6$ are independently are hydrogen; chlorine; fluorine; bromine; methyl; $C_1$-$C_4$ alkoxy, trifluoromethoxy; cyano; nitro; trifluoromethyl; $R^bSO_n$— wherein n is the integer 0 or 2 and $R^b$ is methyl, chloromethyl, trifluoromethyl, $R^cC(O)$— wherein $R^c$ is $C_1$-$C_4$ alkyl; or $SO_2NR^cR^d$ wherein $R^c$ and $R^d$ are as defined and $R^5$ is in the 3-position and $R^6$ is in the 4-position.

4. The compounds of claim 2 wherein R is chlorine or nitro; $R^1$ is methyl or ethoxy; $R^2$ is chlorine or nitro; $R^3$ is hydrogen; $R^4$ is hydrogen; $R^5$ is hydrogen and $R^6$ is hydrogen, chlorine, bromine, fluorine, cyano, trifluoromethyl or $R^bSO_2$ wherein $R^b$ is $C_1$-$C_4$ alkyl or $C_1$-$C_4$ haloalkyl.

5. The compound of claim 2 wherein R is chlorine, $R^1$ is methyl; $R^2$ is hydrogen; $R^3$ is hydrogen; $R^4$ is hydrogen; $R^5$ is hydrogen; and $R^6$ is 4—$SO_2CH_3$.

6. The compound of claim 2 wherein R is nitro; $R^1$ is methyl; $R^2$ is hydrogen; $R^3$ is hydrogen; $R^4$ is hydrogen; $R^5$ is hydrogen; and $R^6$ is 4-chlorine.

7. The compound of claim 2 wherein R is nitro; $R^1$ is methyl; $R^2$ is hydrogen; $R^3$ is hydrogen; $R^4$ is hydrogen; $R^5$ is hydrogen and $R^6$ is hydrogen.

8. The compound of claim 2 wherein R is methyl; $R^1$ is methyl; $R^2$ is hydrogen; $R^3$ is hydrogen; $R^4$ is hydrogen; $R^5$ is hydrogen and $R^6$ is 4—$SO_2C_2H_5$.

9. The compound of claim 2 wherein R is nitro; $R^1$ is methyl; $R^2$ is 2-chlorine; $R^3$ is hydrogen; $R^4$ is hydrogen; $R^5$ is hydrogen and $R^6$ is hydrogen.

10. The compound of claim 2 wherein R is nitro, $R^1$ is methyl; $R^2$ is 2-nitro; $R^3$ is hydrogen; $R^4$ is hydrogen; $R^5$ is hydrogen and $R^6$ is hydrogen.

11. The compound of claim 2 wherein R is nitro; $R^1$ is methyl; $R^2$ is 2-chlorine; $R^3$ is hydrogen; $R^4$ is hydrogen; $R^5$ is hydrogen; and $R^6$ is 4-chlorine.

12. The compounds of claim 2 wherein $R^3$ and $R^5$ are hydrogen.

13. The compounds of claim 3 wherein $R^3$ and $R^5$ are hydrogen.

* * * * *

UNITED STATES PATENT AND TRADEMARK OFFICE
CERTIFICATE OF CORRECTION

PATENT NO. : 4,780,569

DATED : October 25, 1988

INVENTOR(S) : David L. Lee

It is certified that error appears in the above-identified patent and that said Letters Patent is hereby corrected as shown below:

In the abstract, next to the last line; in Column 2, line 13; and in Column 11, line 26, the phrase "$R^e$" should read ---$R^c$---.

Signed and Sealed this

Fifth Day of March, 1991

Attest:

HARRY F. MANBECK, JR.

*Attesting Officer*　　　　*Commissioner of Patents and Trademarks*

UNITED STATES PATENT AND TRADEMARK OFFICE
CERTIFICATE OF CORRECTION

PATENT NO. : 4,780,569
DATED : October 25, 1988
INVENTOR(S) : David L. Lee

It is certified that error appears in the above-identified patent and that said Letters Patent is hereby corrected as shown below:

In Columns 1 and 2, between lines 39-63, in the four structural formulae, the hydrogen atom or proton "H" should be circled.

In Column 5, lines 15-20, formula which reads

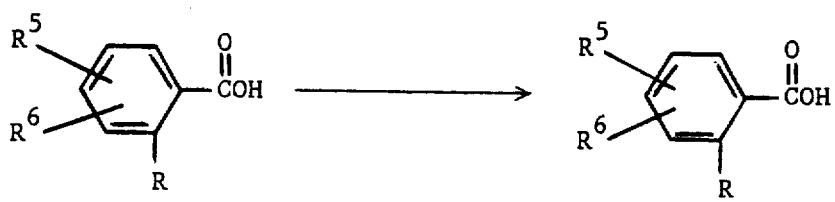

should read

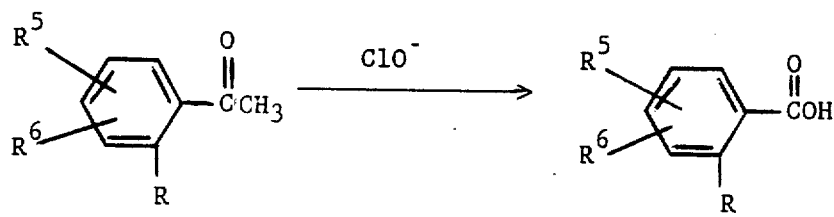

UNITED STATES PATENT AND TRADEMARK OFFICE
CERTIFICATE OF CORRECTION

PATENT NO. : 4,780,569
DATED : October 25, 1988
INVENTOR(S) : David L. Lee

It is certified that error appears in the above-identified patent and that said Letters Patent is hereby corrected as shown below:

In Column 6, Table 1, for Comp. No. $4^a$, the entry under column $R^6$ should read ---H--- and the entry under m.p. °C. should read 99-103.

In Column 10, line 63, the word "abovedescribed" should read ---above-described---.

Signed and Sealed this

Twenty-fourth Day of December, 1991

Attest:

HARRY F. MANBECK, JR.

*Attesting Officer*     *Commissioner of Patents and Trademarks*